US00PP37774P2

(12) United States Plant Patent
Hartman

(10) Patent No.: US PP37,774 P2
(45) Date of Patent: Oct. 13, 2026

(54) ***CALADIUM* PLANT NAMED 'VIC OF14-1158'**

(50) Latin Name: ***Caladlium* X *hortulanum***
Varietal Denomination: VIC OF14-1158

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 19/639,807

(22) Filed: Apr. 6, 2026

(51) Int. Cl.

| | |
|---|---|
| ***A01H 5/12*** | (2018.01) |
| ***A01H 5/02*** | (2018.01) |
| ***A01H 6/10*** | (2018.01) |

(52) U.S. Cl.
USPC ..... Plt./373
CPC ..... *A01H 6/10* (2018.05)

(58) Field of Classification Search
USPC ..... Plt./373
CPC ..... A01H 5/12; A01H 5/02
See application file for complete search history.

*Primary Examiner* — Kent L Bell
(74) *Attorney, Agent, or Firm* — C. Anne Whealy

(57) ABSTRACT

A new and distinct cultivar of *Caladium* plant named 'VIC OF14-1158', characterized by its upright and mounding plant habit and relatively short in height; dense, leafy and bushy appearance; vigorous growth habit and rapid growth rate; ruffled lance-type leaves that are mostly purplish red in color with dark green variegated margins; and petioles that are tannish pink in color with faint brown-colored stippling, stripes, streaks and tessellations.

4 Drawing Sheets

Figure 1:
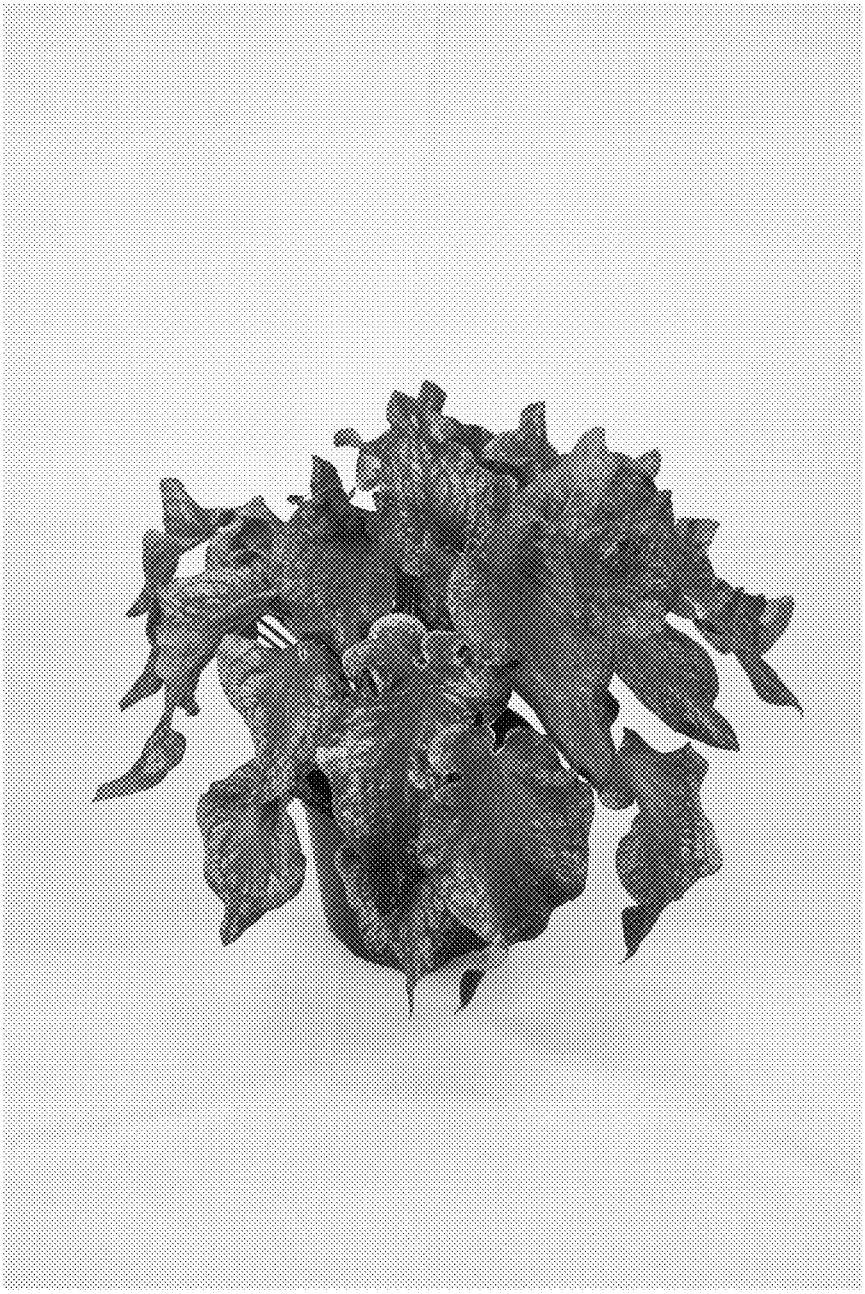

Botanical designation: *Caladium* X *hortulanum*.
Cultivar denomination: 'VIC OF14-1158'.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'VIC OF14-1158'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2013 in Avon Park, Florida of *Caladium* X *hortulanum* 'Victoria', disclosed in U.S. Plant Pat. No. 18,087, as the female, or seed, parent with *Caladium* X *hortulanum* 'Lemon Blush', disclosed in U.S. Plant Pat. No. 25,450, as the male, or pollen, parent. The new *Caladium* plant was discovered and selected by the Inventor as a single plant within the progeny of the stated cross-pollination in a controlled outdoor nursery environment in Avon Park, Florida in September, 2014.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Florida since April, 2015 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'VIC OF14-1158'. These characteristics in combination distinguish 'VIC OF14-1158' as a new and distinct *Caladium* plant:

1. Upright and mounding plant habit and relatively short in height; dense, leafy and bushy appearance.
2. Vigorous growth habit and rapid growth rate.
3. Ruffled lance-type leaves that are mostly purplish red in color with dark green variegated margins.
4. Petioles that are tannish pink in color with faint brown-colored stippling, stripes, streaks and tessellations.

Plants of the new *Caladium* differ primarily from plants of the female parent, 'Victoria', in the following characteristics:

1. Plants of the new *Caladium* are more vigorous than plants of 'Victoria'.
2. Potted plants of the new *Caladium* finish about two to three weeks earlier than potted plants of 'Victoria'.
3. Leaves of plants of the new *Caladium* are mostly purplish red in color with dark green variegated margins, whereas leaves of plants of 'Victoria' are rose pink in color suffused with greenish white with rose pink venation.

Plants of the new *Caladium* differ primarily from plants of the male parent, 'Lemon Blush', in the following characteristics:

1. Plants of the new *Caladium* produce lance-type leaves whereas plants of 'Lemon Blush' produce fancy-type leaves.

2. Leaves of plants of the new *Caladium* are more rugose and ruffled than and have more undulating margins than leaves of plants of 'Lemon Blush'.
3. Leaves of plants of the new *Caladium* are mostly purplish red in color with dark green variegated margins, whereas leaves of plants of 'Lemon Blush' are chartreuse to lime green in color with rose red-colored centers.

Plants of the new *Caladium* can be compared to plants of *Caladium* X *hortulanum* 'Tiki Torch', disclosed in U.S. Plant Pat. No. 26,264. In side-by-side comparisons, plants of the new *Caladium* differ primarily from plants of 'Tiki Torch' in the following characteristics:

1. Leaves of plants of the new *Caladium* are more rugose and ruffled than leaves of plants of 'Tiki Torch'.
2. Leaves of plants of the new *Caladium* are mostly purplish red in color with dark green variegated margins, whereas leaves of plants of 'Tiki Torch' have rose red-colored centers and venation with lime green to chartreuse-colored margins.

Plants of the new *Caladium* can also be compared to plants of *Caladium* X *hortulanum* 'Scarlet Flame', disclosed in U.S. Plant Pat. No. 25,419. In side-by-side comparisons, plants of the new *Caladium* differ primarily from plants of 'Scarlet Flame' in the following characteristics:

1. Leaves of plants of the new *Caladium* are more rugose and ruffled than leaves of plants of 'Scarlet Flame'.
2. Leaves of plants of the new *Caladium* are mostly purplish red in color with dark green variegated margins, whereas leaves of plants of 'Scarlet Flame' are dark green in color with rose red-colored venation and pink and rose red-colored spots and blotches.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'VIC OF14-1158' grown in a container that has not had its tuber de-eyed prior to planting.

Figure 2:
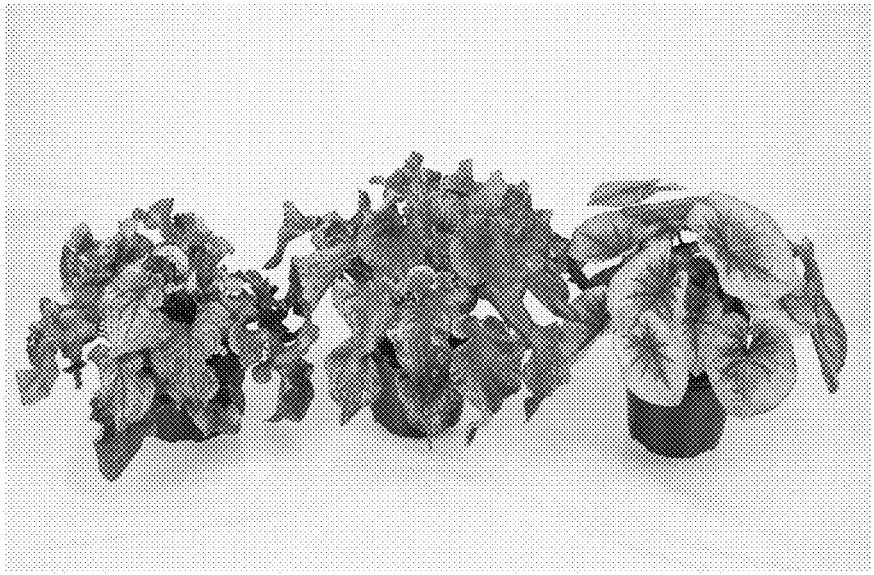

The photograph at the top of the second sheet (FIG. 2) is side perspective view of typical plants of the female parent, 'Victoria' (left), 'VIC OF14-1158' (center) and the male parent, 'Lemon Blush' (right).

Figure 3:
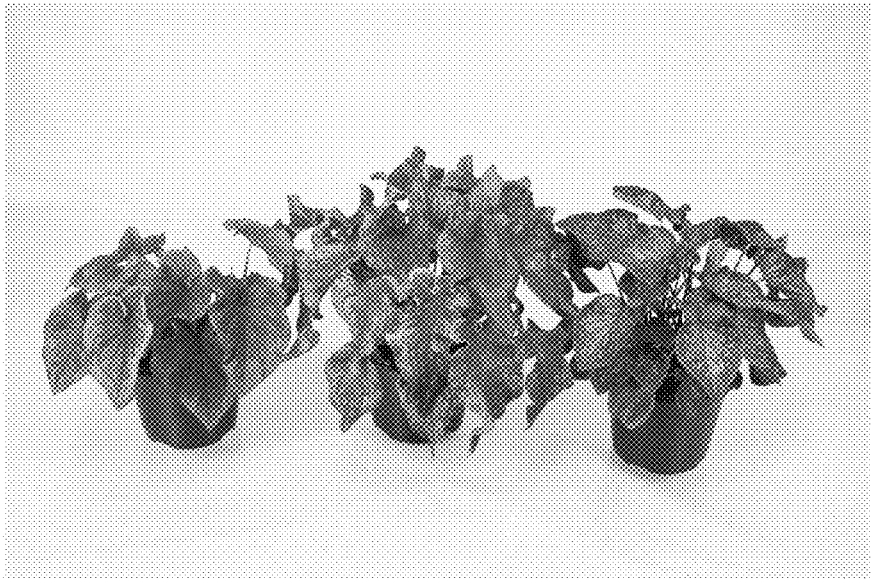

The photograph at the bottom of the second sheet (FIG. 3) is side perspective view of typical plants of 'Tiki Torch' (left), 'VIC OF14-1158' (center) and 'Scarlet Flame' (right).

Figure 4:
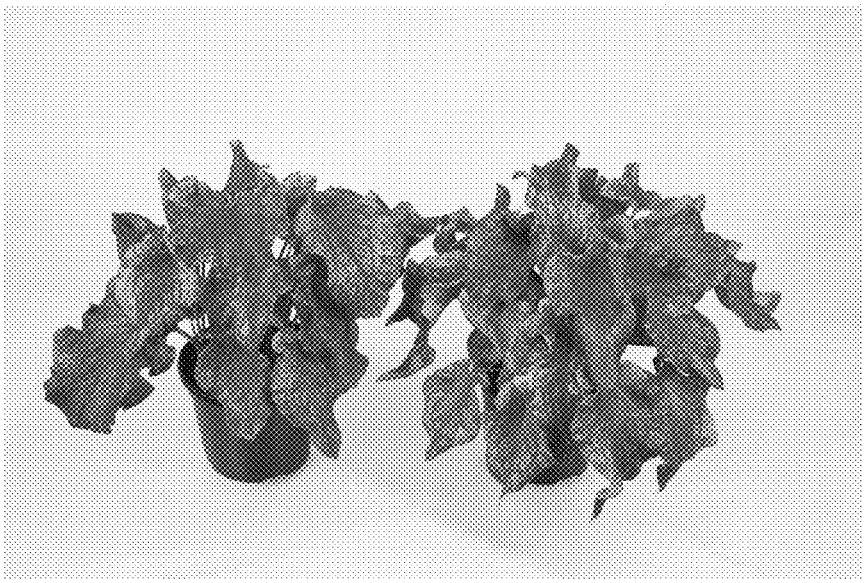

The photograph at the top of the third sheet (FIG. 4) is a comparison view of typical plants of 'VIC OF14-1158' grown in containers, the plant on the left has not had its tuber de-eyed and the plant on the right has had its tuber de-eyed prior to planting.

Figure 5:
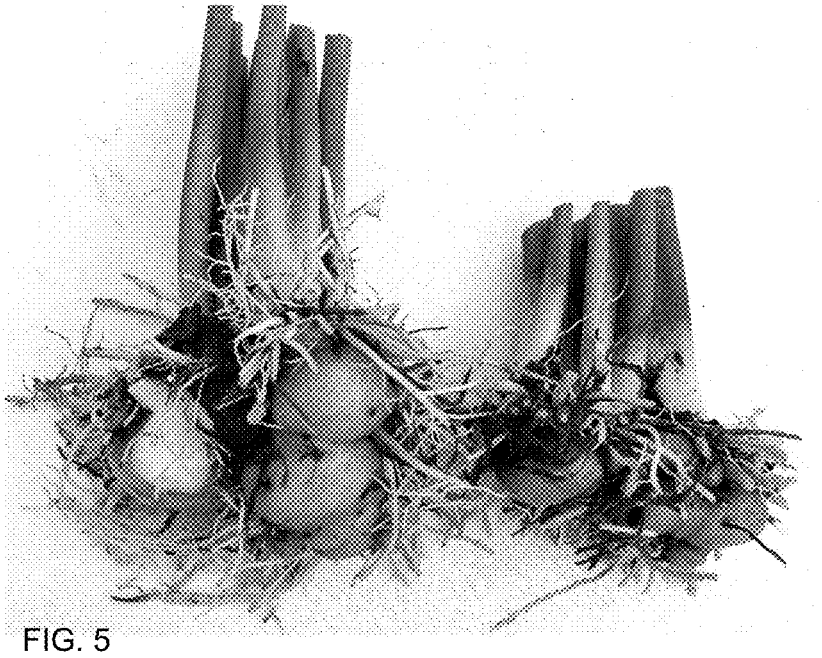

The photograph at the bottom of the third sheet (FIG. 5) is a close-up view of freshly-harvested tubers with roots of 'VIC OF14-1158'.

Figure 6:
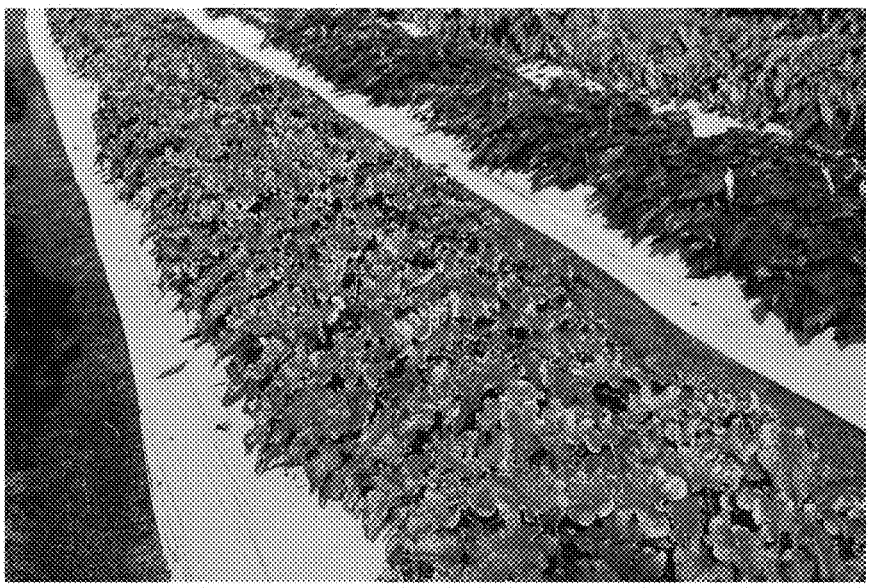

The photograph at the top of the fourth sheet (FIG. 6) is a side perspective view of typical field-grown plants of 'VIC OF14-1158'.

Figure 7:
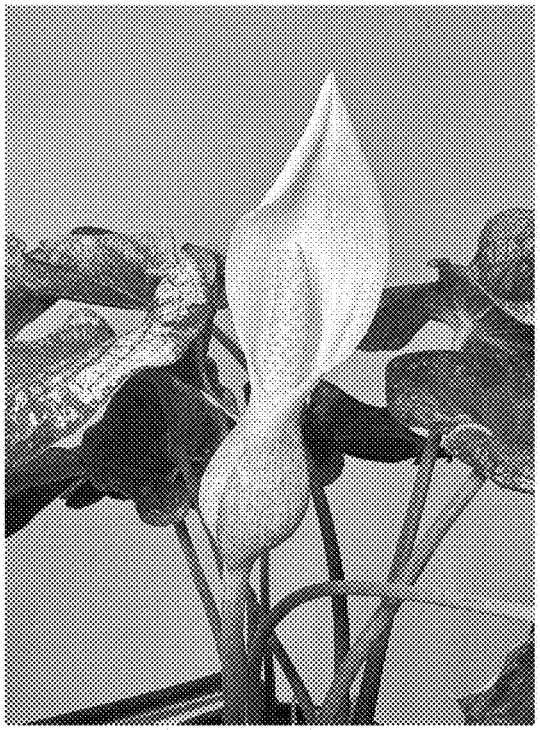

The photograph at the bottom of the fourth sheet (FIG. 7) is a close-up view of a typical inflorescence of 'VIC OF14-1158'.

DETAILED BOTANICAL DESCRIPTION

The aforementioned photographs and following observations and measurements describe plants grown in 15-cm containers in a polypropylene-covered shade house (50% light reduction) in Avon Park, Florida and plants grown in ground beds under full sunlight conditions in an outdoor nursery in Zolfo Springs, Florida. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and under full sunlight conditions. Plants grown in the shade house were about nine weeks old and plants grown in the outdoor nursery were about seven months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'VIC OF14-1158'.

Parentage:

*Female, or seed, parent.*—*Caladium* X *hortulanum* 'Victoria', disclosed in U.S. Plant Pat. No. 18,087.

*Male, or pollen, parent.*—*Caladium* X *hortulanum* 'Lemon Blush', disclosed in U.S. Plant Pat. No. 25,450.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented and branched; individual segments are elliptic, ovate to irregular in shape. Height: About 2.6 cm to 3 cm. Diameter, largest width: About 4.5 cm to 7 cm. Segment height: About 2.3 cm to 2.7 cm. Segment diameter: About 2.5 cm to 3 cm. Axillary bud shape: Roughly triangular, flattened. Axillary bud height: About 3 mm. Axillary bud width: About 3.5 mm. Texture: Thick, starchy; somewhat brittle. Color: Periderm, freshly-harvested: Close to 199C and 199D. Periderm, dried: Close to 200A. Epidermis: Close to N170D. Cortical tissue: Close to 6D, 10D and NN155A. Axillary buds: Close to 38C. Root description: Relatively thick, fleshy contractile roots with few lateral branches; color, close to NN155B, NN155C and NN155D; actual color of the roots is dependent on substrate composition, water quality, fertilizer type and formulation, substrate temperature and physiological age of roots; root density, dense.

Plant description:

*Plant type*.—Herbaceous perennial; suitable as a potted plant in containers 15-cm to 25-cm and suitable as a landscape plant in shaded landscape areas.

*Plant and growth habit*.—Upright and mounding plant habit and relatively short in height; dense, leafy and bushy appearance; vigorous growth habit and rapid growth rate; potted plants finish in saleable form in about six to seven weeks after planting tubers; leaf petioles and leaves arise from one or more growing points on tubers; leaf petioles initially upright and leaning outwardly to arching with development.

*Plant height, from soil level to top of foliar plane, shade house-grown potted plants, tubers de-eyed*.—About 16 cm to 20 cm.

*Plant height, from soil level to top of foliar plane, shade house-grown potted plants, tubers not de-eyed*.—About 16 cm to 24 cm.

*Plant height, from soil level to top of inflorescences*.—About 26 cm.

*Plant diameter, shade house-grown potted plants, tubers de-eyed and not de-eyed*.—About 32 cm to 39 cm.

*Number of shoots per plant, shade house-grown potted plants, tubers de-eyed*.—About five to nine develop per #1 tuber.

*Number of shoots per plant, shade house-grown potted plants, tubers not de-eyed*.—About three to five develop per #1 tuber.

*Cataphylls, shade house-grown potted plants*.—Length: About 4.5 cm to 5.6 cm. Width: About 1 cm to 1.5 cm. Shape: Wedge-shaped. Apex: Acute. Base: Sheathing the stem. Texture, outer and inner surfaces: Smooth, glabrous. Color, mature outer and inner surfaces: Close to 200A to 200B development.

Leaf description:

*Arrangement and type*.—Alternate; simple; lance-type.

*Length, shade house-grown potted plants, tubers de-eyed*.—About 11.5 cm to 16 cm.

*Width, shade house-grown potted plants, tubers de-eyed*.—About 7.5 cm to 9 cm; when flattened, about 7 cm to 11 cm.

*Length, shade house-grown potted plants, tubers not de-eyed*.—About 11.5 cm to 20.4 cm.

*Width, shade house-grown potted plants, tubers not de-eyed*.—About 7.6 cm to 11.6 cm; when flattened, about 8 cm to 13 cm.

*Shape*.—Ovate to broadly elliptic.

*Apex*.—Acute.

*Base*.—Sagittate, sagittate-peltate or cordate, lobes often imbricate.

*Margin*.—Entire, with broad undulations.

*Texture and luster, upper surface*.—Rugose and ruffled, glabrous; dull sheen.

*Texture and luster, lower surface*.—Rugose and ruffled, glabrous; slightly glaucous in center and around venation, dull sheen.

*Venation pattern*.—Pinnate and palmate.

*Color, shade house-grown potted plants*.—Developing leaves, upper surface: Interveinal areas: Variably flushed or entirely close to 59C, 59D, 58C, 159D, 137B, 187C and N170D. Margins, distally: Close to NN137A and 137A; narrow marginal edges, close to 187C. Margins, proximally: Close to 146D, 194C, 159B and 159C variably tinged with close to 187C. Basal notch: Close to 160D and 187B. Midvein and primary venation: Close to 53A; surrounded with close to 53D. Lateral venation: Close to 59A and 187C. Developing leaves, lower surface: Interveinal areas: Close to 184C, 184D, 59C, 194B, 194C, 194D and 159D. Margins, distally: Close to 148B and 148C; narrow marginal edges, close to 187B. Margins, proximally: Close to 194B, 194C and 159D flushed with close to 187D. Basal notch: Close to 147D tinged with close to 187B. Midvein: Close to 159B and 159C tinged with streaks, close to 185C; surrounded with close to 185D. Lateral venation: Close to 147A. Fully expanded leaves, upper surface: Interveinal areas: Variably flushed or entirely close to 59C, 59D, 58C, 159D, 137B, 187C and N170D. Margins, distally: Close to NN137A and 137A; narrow marginal edges, close to 187C. Margins, proximally: Close to 147A, 146B, 194C, 159B and 159C variable tinged with close to 187C. Basal notch: Close to 160D and 187B. Midvein and primary venation: Close to 53A; surrounded with close to 53D. Lateral venation: Close to 59A and 187C. Fully expanded leaves, lower surface: Interveinal areas: Close to 184C, 184D, 59C, 194B, 194C, 194D and 159D. Margins, distally: Close to 148B and 148C; narrow marginal edges, close to 187B. Margins, proximally: Close to 194A, 194B, 194C 159D, 148B and 148C flushed with close to 187D. Basal notch: Close to 147D tinged with close to 187B. Midvein: Close to 159B and 159C tinged with streaks, close to 185C; surrounded with close to 185D. Lateral venation: Close to N187B, 59B and 59C tinged with close to 185C; surrounded by close to 185D.

*Petioles*.—Aspect: Initially upright and straight and leaning outwardly to arching with development; flexible. Length, shade house-grown potted plants, tubers de-eyed: About 10.5 cm to 16.5 cm. Diameter, distally, shade house-grown potted plants, tubers de-eyed: About 2 mm to 3.5 mm. Diameter, proximally, shade house-grown potted plants, tubers de-eyed: About 3.5 mm to 5.2 mm. Length, shade house-grown potted plants, tubers not de-eyed: About 10.3 cm to 26 cm. Diameter, distally, shade house-grown potted plants, tubers not de-eyed: About 3.5 mm to 4.8 mm. Diameter, proximally, shade house-grown potted plants, tubers not de-eyed: About 4.2 mm to 7 mm. Texture and luster: Smooth, glabrous; glaucous. Color, shade house-grown potted plants: When developing and developed: Close to 147C, 147D and 146D faintly tinged with close to 177D and 182D with stippling, streaks and tessellations, close to 200A and 200B; just below the leaf junction, close to 182D and 195B with faint stippling and streaks, close to 200D; or may be close to 147D tinged with close to 182D with faint stippling, close to 200D. Wing length, shade house-grown potted plants: About 3 cm to 3.9 cm. Wing diameter, shade house-grown potted plants: About 5.1 mm to 6 mm. Texture and luster, outer and inner surfaces: Smooth, glabrous; dull to slightly glossy. Wing color, shade house-grown potted plants: Outer surface: Close to 195B tinged with close to 182D with stippling, streaks and tessellations, close to 200A and 200B. Inner surface: Close to N155D tinged with close to 194B; venation, close to 200A; colors and patterns from the outer surface are visible on the inner surface.

Inflorescence description:

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring and summer in central Florida; flowers develop about seven weeks after growth commences; inflorescences last about three days before fading; inflorescences persistent.

*Spathe*.—Length, overall: About 11.2 cm. Length, distal open portion: About 7.6 cm. Length, proximal closed portion: About 3.6 cm. Width, distal open portion: About 3.5 cm. Depth, distal open portion: About 1.2 cm. Width, at constriction: About 1.2 cm to 1.7 cm. Width, proximal closed portion: About 2.5 cm. Shape, open portion: Elliptic. Apex: Acute to acuminate. Base: Acute. Margin: Entire, slightly reflexed. Texture and luster, front surface: Smooth, glabrous; dull sheen. Texture and luster, rear surface: Smooth, glabrous; dull sheen and slightly glaucous. Color, front surface: Distal open portion: Close to 155C; with subsequent development, color becoming closer to 199A. Proximal closed portion: Close to 148C to 148D, at the base, flushed with close to N186C; colors do not change with subsequent development. Color, rear surface: Distal open portion: Close to 145C to 145D with streaks, close to 145B; colors do not change with subsequent development. Proximal closed portion: Close to 194C and 194D; streaks and lightly mottled with close to 146B; colors do not change with subsequent development.

*Spadix*.—Length, overall: About 6.9 cm. Length, sterile zone: About 1.4 cm. Length, female flower zone: About 1.5 cm. Diameter, male flower zone: About 8 mm. Diameter, sterile flower zone: About 5 mm. Diameter, female flower zone: About 9 mm. Shape: Columnar, spindle-shaped. Apex: Obtuse to bluntly acute. Base: Obtuse. Aspect: Upright. Color, mature, male zone: Close to 159D faintly tinged with close to 145D. Color, mature, sterile zone: Close to 159D. Color, mature, female zone: Stigmas, close to 159A; ovaries, close to N170D. Male flowers: Quantity per spadix: About 200. Shape: Obovate. Height: About 2.8 mm. Diameter: About 3 mm. Pollen amount: Moderate. Pollen color: Close to 11C. Female flowers: Quantity per spadix: About 245. Shape: Obovate. Height: About 2.8 mm. Diameter: About 1.5 mm. Stigma color: Close to 159A. Ovary color: Close to N170D.

*Scapes*.—Length: About 14.9 cm. Diameter: About 5 mm. Strength: Sturdy; flexible. Aspect: Mostly erect, straight. Texture and luster: Smooth, glabrous; proximally, slightly glossy; distally, slightly glaucous. Color: Close to 147B and 147C with streaks, close to 147A; distally, close to 147C and 147D with streaks, close to 147B.

*Seeds and fruits*.—To date, seed and fruit development have not been observed on plants of the new *Caladium*.

Pathogen tolerance/resistance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'VIC OF14-1158' as herein illustrated and described herein.

* * * * *